United States Patent [19]

Shigezawa et al.

[11] Patent Number: 6,143,020

[45] Date of Patent: Nov. 7, 2000

[54] AIR WARMING SYSTEM FOR PROVIDING A CONTROLLED TEMPERATURE OF AIR TO AN AIR BLANKET

[75] Inventors: Gordon Shigezawa, Irvine; Anthony V. Beran, Santa Ana, both of Calif.

[73] Assignee: Respiratory Support Products, Inc., Irvine, Calif.

[21] Appl. No.: 09/113,630

[22] Filed: Jul. 10, 1998

[51] Int. Cl.$^7$ .................................. A61F 7/12; A61F 7/00
[52] U.S. Cl. ............................. 607/96; 607/104; 607/107
[58] Field of Search ..................................... 607/104, 107, 607/96, 108, 112

[56] References Cited

U.S. PATENT DOCUMENTS

| | | |
|---|---|---|
| 2,110,022 | 3/1938 | Kliesrath . |
| 2,601,189 | 6/1952 | Wales, Jr. . |
| 2,706,988 | 4/1955 | Weber . |
| 4,660,388 | 4/1987 | Greene, Jr. . |
| 5,300,102 | 4/1994 | Augustine . |
| 5,324,320 | 6/1994 | Augustine et al. . |
| 5,383,918 | 1/1995 | Panetta ..................................... 607/104 |
| 5,405,371 | 4/1995 | Augustine et al. . |
| 5,545,196 | 8/1996 | Falk ........................................ 607/105 |
| 5,634,940 | 6/1997 | Panyard ................................... 607/104 |
| 5,733,320 | 3/1998 | Augustine ............................... 607/107 |
| 5,876,428 | 3/1999 | Van Duren .............................. 607/107 |

OTHER PUBLICATIONS

Brochure for Bair Hugger Cub Blanket, Augustine Medical, Inc. 1993.
Brochure for Bair Hugger Chest Access Blanket, Augustine Medical, Inc., 1992.
Brochure for Bair Hugger Torso Blanket Model 530, Augustine Medical, Inc., Jan. 1, 1993.
Brochure for Bair Hugger Multi–Access Blanket, Augustine Medical, Inc. 1992.
Brochure and Operations Manual for Bair Hugger Warming System, Model 200, Augustine Medical, Inc., 1993.
Brochure for Advanced Bair Hugger Patient Warming System, Augustine Medical, Inc., 1993.
Brochure for 241 Fluid Warming, Augustine Medical, Inc., 1994.
Brochure for Thermacare Patient Comfort System, Gaymar Industries, Inc., 1992.
Brochure for The Warm Air Warming Tube, Bimeco, May 1993.

*Primary Examiner*—Linda C. M. Dvorak
*Assistant Examiner*—Roy Gibson
*Attorney, Agent, or Firm*—Price and Gess

[57] ABSTRACT

A fluid blanket warming system for a patient includes a thermal blanket unit for receiving heated gas through a coupling port. A portable heat source includes a heater unit and a blower unit that are controlled by a control circuit for providing a desired output to temperature to a patient. A flexible conduit delivers the heated gas from the heat source to the thermal blanket. A temperature sensor unit can be mounted adjacent the thermal blanket unit and in contact with the gas received from the heater unit to provide a temperature signal representative of the heated gas. The temperature sensor unit can be mounted directly on the thermal blanket, on the coupler of the flexible conduit, or on a modular coupler to provide a temperature signal to the control circuit.

32 Claims, 4 Drawing Sheets

AIR WARMING SYSTEM FOR PROVIDING A CONTROLLED TEMPERATURE OF AIR TO AN AIR BLANKET

BACKGROUND OF THE INVENTION

1. Field of the Invention

The present invention is directed to an air blanket warming system for incorporating a remote temperature sensor mounted adjacent the air blanket to provide a temperature signal representative of the heated air delivered to the air blanket and includes an improved conduit unit, remote temperature sensor unit, and improved air blanket.

2. Description of Related Art

It is well known to provide heated air to portions of the human body to maintain the human body temperature and/or to provide curative heat treatment to a patient. Air blankets are frequently used in operating rooms and critical care units and include a disposable air blanket that can be formed from a thin plastic or thin plastic paper configuration with appropriate apertures on one side of the blanket to bathe a patient with warm air. During the operation, the temperature of the patient can therefore be controlled. In a post-operative setting, it is possible to treat the patient for hypothennia. The concepts and use of the application of both heated and cold air is well known such as shown in U.S. Pat. No. 2,110,022 and U.S. Pat. No. 2,601,189.

Air blankets or thermal blankets generally use a heater unit that is portable and includes a cabinet having operator controls for setting temperatures with an internal heater unit and blower unit for delivering a controlled temperature of air to a flexible conduit. The flexible conduit extends from the cabinet to the thermal blanket. A temperature sensor is mounted at the egress of the cabinet housing to measure the heated air for purposes of controlling the heater unit within the housing. The flexible conduit is replaceable and connects to an appropriate coupler port on an inflatable thermal blanket. The blanket is disposable and is usually offset from the heater or source cabinet by a distance of approximately 24 to 36 inches of flexible hose length. The temperature sensor that is within the cabinet is physically and thermally isolated from the inflatable blanket by the hose and also frequently by interspaced components such as filters and connectors.

The flexible hose diameter is typically 2½ inches and the air flow velocity is from a range of 1200 to 2000 feet a minute. The temperature of the warm air delivered to the flexible hose ranges from approximately ambient temperature to 48 degrees Centigrade. If the room temperature is about 20 degrees Centigrade, there is a drop of about 4 degrees Centigrade that can occur at the highest delivered air temperature as the air flows in the hose to the thermal blanket. This temperature drop, however, is highly dependent on not only the room temperature but also any turbulence generated in the hose air flow due to bends in the hose. Additional descriptions of thermal blankets can be found for example in U.S. Pat. Nos. 5,324,320, and 4,660,388.

The prior art is still seeking to improve the warming air apparatus for addressing the issue of hypotherapy in patients undergoing surgery and to further assist in the re-warming process after surgery or prolonged exposure to cold environment.

OBJECTS AND SUMMARY OF THE INVENTION

The present invention provides a fluid blanket warming system or thermal blanket system that can be applied to a patient to address hypothermia and includes a blanket unit made of a light weight material such as plastic and/or plastic and paper having an approximately hollow core to form a plenum chamber for the receiving of a gas such as heated air. A coupling port is provided to enable the admission of the gas from a heat source. Generally, the heat source is in a portable housing cabinet that supports a heater unit for heating the gas and a blower unit for providing forced air to the heater unit. A control circuit controls the temperature of the heater unit and the air can be filtered as it enters into the cabinet and also as it leaves the cabinet. A flexible conduit can be removably connected to a port on the cabinet housing for the delivery of the heated gas to an inflatable blanket unit. The inflatable blanket unit can come in various configurations and shapes and can include segmented or channel sections to assist in erecting the blanket when it is heated. The inner surface of the thermal blanket adjacent to the patient will be porous to thereby pass the thermally controlled air to the appropriate application of the patient's body. Regardless of the particular configuration or construction of the thermal blanket, it will have a coupling port for removable connection with the flexible conduit.

A temperature sensor unit is mounted adjacent the thermal blanket unit and is in direct contact with the heated gas received from the heater unit to provide a temperature signal that is representative of the heated gas, such as air, as it is delivered to the thermal blanket unit. The control circuit thereby can drive a heater unit and blower unit within the cabinet to provide a pre-determined temperature for the patient which will take into account any temperature loss from the heater unit across the flexible conduit to the thermal blanket.

In one embodiment of the invention, the temperature sensor unit can be mounted within a coupler that can connect to the coupling port of the thermal blanket. The temperature sensor unit can include a heat conductive support member extending across the flow path of the heated gas so that the temperature sensor can accurately respond to the actual temperature. This heat conductor member can be in the form of a cross arm configuration that is structurally formed from a plastic resin substrate cladded with a heat conductive metal, such as copper, stainless steel, nickel, etc. The temperature sensor unit can be mounted at the inter-connection or junction of the arm members and since the heat conductive arms extend across the flow path, it can accurately average the temperature regardless of laminar or turbulent flow at the entrance to the thermal blanket.

An alternative embodiment of the invention can have the temperature sensor unit mounted directly on a coupler that can be removably attached to a thermal blanket rather than having it attached to a coupler on a flexible conduit.

A further alternative embodiment can have the temperature sensor unit directly mounted on the thermal blanket.

In an embodiment of the invention, a conduit unit for fluidly inter-connecting a thermal blanket with a housing having a heater unit can comprise an elongated flexible conduit with a first coupler at one end of the conduit configured for removable connection to the heater housing and a second coupler at the opposite end of the conduit configured for removable connection to the air blanket or thermal blanket. A temperature sensor unit is mounted to sense the temperature of the air heated by the heater unit as it exits the second coupler. An electrical connector can extend from the temperature sensor unit through the first coupler and can have an end or terminal portion adapted to be electrically connected to transmit a temperature signal from the temperature sensor unit to a control circuit so that the heater unit can be controlled to a pre-determined temperature for a patient.

Finally, a second temperature sensor can also be mounted to provide a redundant measurement adjacent the first temperature sensor and a safety alarm circuit can shut off the air warming system, if the temperature level extends beyond predetermined limits.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved temperature sensor unit for a fluid warming system that can be applied to a flexible conduit, a coupler, and a thermal blanket.

The present invention recognizes that the temperature measurement which is most important in a fluid blanket warming system for a patient such as an air blanket or thermal blanket warming system is the temperature in the proximity of the patient's skin. The present invention is an attempt to approximate that temperature by measuring the heated air as it is delivered to the thermal blanket in an economical manner. While the present invention is disclosed with a conventional heater unit for heating ambient air, it can be recognized that the heating of other gases that may have a treatment impact upon the patient is also possible. The present invention discloses a schematic form of a heat source and more specifics can be found in the inventors' co-pending U.S. Pat. No. 5,785,723, filed on Oct. 23, 1995, which is incorporated herein by reference.

The present invention is primarily designed to provide an improvement in the treatment of hypothermia which occurs when a patient's body core temperature drops below 36 degrees Centigrade. A large percentage of patients undergoing operative procedures can become hypothermic. Some of the factors that contribute to this condition include the cold operating room environment that is favored by surgeons, the anesthetic drug effect and the consequences of opening up of a body cavity of a patient. Some of the adverse consequences of hypothermia can include coagulopathy, haemodynamic instability, immunal depression, shivering and discomfort of the patient, altered drug effect, and post-operative nitrogen wasting.

Figure 1:
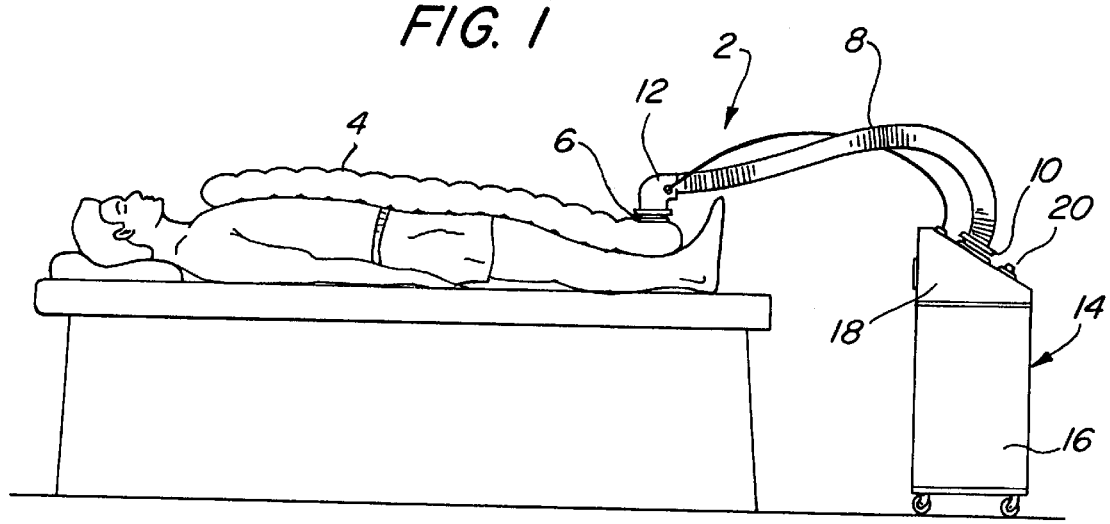
FIG. 1 is a perspective view of a fluid or thermal blanket warming system with a partial cross sectional view of the thermal blanket.

Referring to FIG. 1, a fluid blanket warming system 2 is disclosed. A schematic cross-sectional view of a blanket unit 4 is disclosed. The blanket unit 4 is sometimes referred to as a thermal blanket, inflatable blanket or air blanket and can be subjectively configured to address substantially all or selected portions of a patient's body. The blanket unit 4 can be configured with seams and can have air slits or holes on the underside to deliver the fluid such as heated air or other gases to the patient when inflated. Generally, the blanket unit 4 provides an air plenum of approximately a hollow core for receiving the heated air and distributing it to the patient's body. Frequently, the air blanket is divided, however, into segments or conduits to assist in erecting the air blanket as a canopy across the patient's body. The specific form of the blanket as it is adapted to a portion of the patient's body is not a feature of the present invention and numerous different examples exist and are well known by persons of skill in this field. Thus, the blanket shown in FIG. 1 is for schematic purposes only and does not represent any limitation to the air blankets or thermal blankets that can be utilized in the present invention.

The flexible conduit 8 is usually formed of a flexible plastic material that is corrugated and has a first coupler 10 at one end of the conduit configuration, and a second coupler 12 at the other end of the conduit configuration. A heat source 14 includes a heater housing or cabinet 16 that is mounted for portability with wheels at the bottom. The upper portion of the housing 16 supports a console 18 with operator temperature controls 20.

Figure 2:
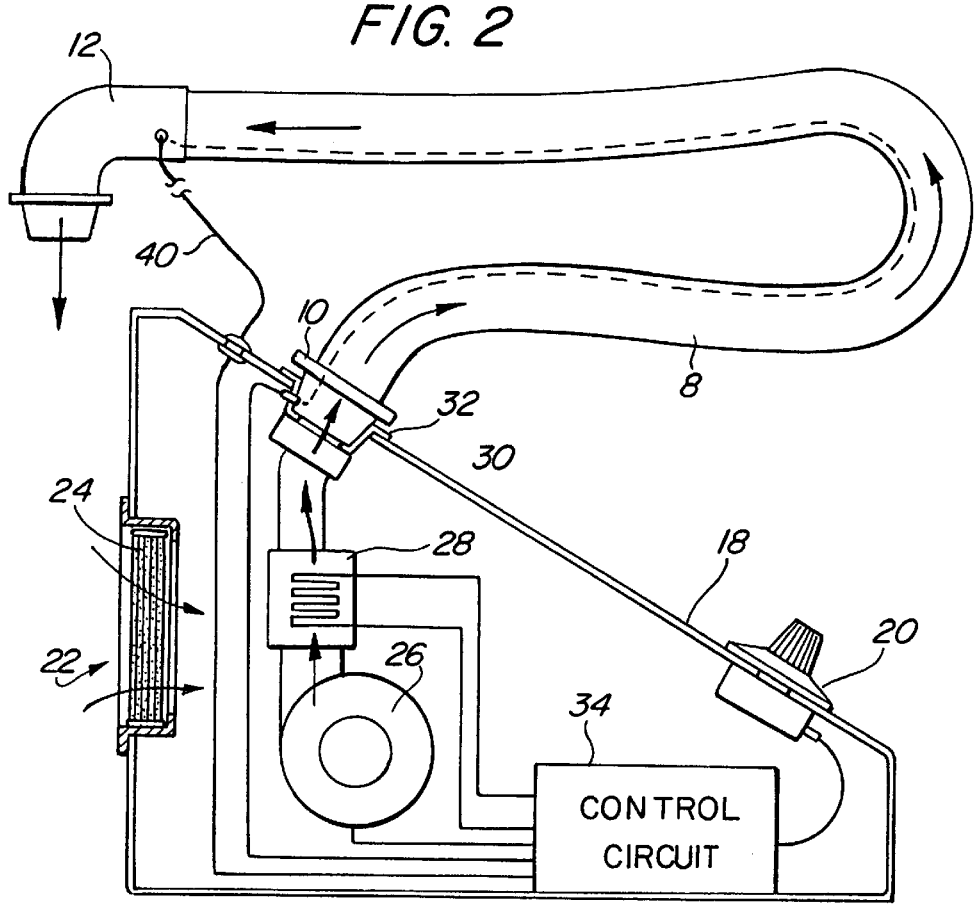
FIG. 2 is a partial cross-sectional view of an air warming system of the present invention.

Referring to FIG. 2, the console 18 includes an inlet port 22 with a filter 24 for drawing air into the cavity of the console 18. A blower unit 26 creates a positive pressure to provide air to a heater unit 28. In the embodiment of FIG. 2, ambient air is being used as the heated fluid for application to the thermal blanket 4. It is possible, however, to provide other gases, if desired. Various configurations of blower, scroll compressor, fans, etc. can be used to provide a positive air pressure. Likewise, the heater unit can also have different configurations than the resistance heater coils shown.

Downstream of the heater unit 28, a gas filter 30 can be positioned, and the conduit from the filter 30 can be connected to a coupler 32 on the console 18. The second filter 30 provides extra filtration but could be eliminated, if desired. The coupler 32 is permanently mounted on the console 18, and the first coupler 10 on the flexible conduit 8 can be removably connected to coupler 32.

Figure 3:
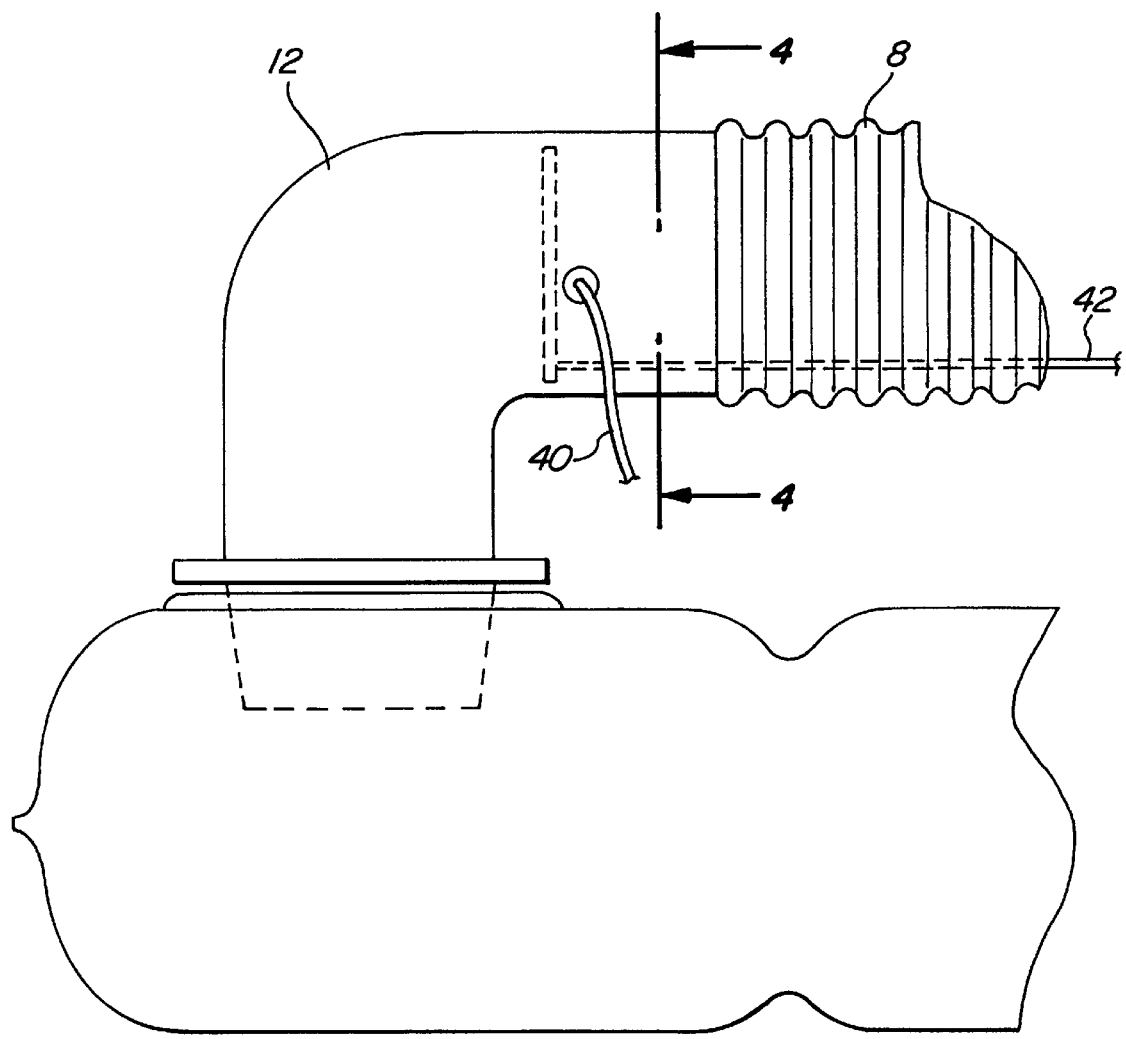
FIG. 3 represents a partial cross-sectional view of the coupling of the flexible conduit to a coupling port of a thermal blanket.
Figure 4:
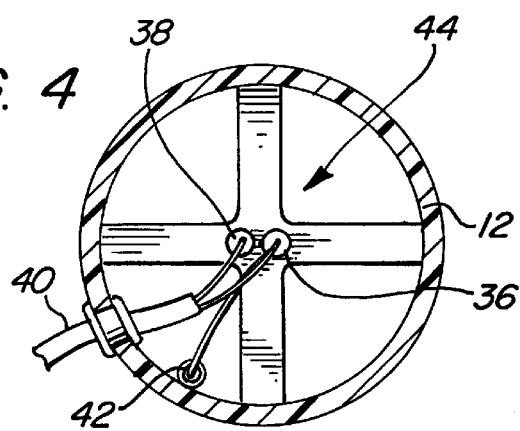
FIG. 4 represents a cross-sectional view of a temperature sensor and housing as shown in FIG. 3.

A control circuit 34 is connected, respectively, to the blower unit 26, the heater unit 28, and a first temperature sensor unit 36. In a first embodiment, the first temperature sensor unit 36 can be mounted within a housing in the form of a coupler 12, as seen in FIGS. 3 and 4.

A second temperature sensor unit 38 can also be mounted on the housing of the second coupler 12 and connected to the control circuit 34 to provide a backup or redundancy for safety purposes, as will be subsequently described.

As shown in FIG. 2, the second sensor unit 38 can have an exterior electrical connector line 40 that can be mounted by plug into a receptacle on the exterior of the console housing 18. Also, as shown in FIGS. 3 and 4, the first sensor unit 36 is connected to an electrical connector line 42 that can travel along an interior of the flexible conduit 8. As can be appreciated, the electrical connector line 40 can also be mounted to extend along the interior of the flexible conduit 8 and, if desired, they can be fastened or adhered to the internal surface of the conduit 8. As shown in FIG. 2, the connector line 42 from the first sensor unit 36 can connect with an appropriate plug or receptacle in the coupler 32 on the console 18 for connection with the control circuit 34.

By providing the first sensor 36 and the second sensor 38 in the second coupler 12, the temperature of the heated air, as it is delivered to the thermal blanket 4, can be accurately measured. Any bends in the flexible conduit 8 that may effect a temperature drop, will occur upstream of the second coupler 12 and heat loss from the flexible conduit 8 will be accounted for.

Since the temperature measured by the respective sensors 36 and 38 can be sensitive to their particular location in the cross-sectional air flow, the present invention provides a mounting structure 44 which can, for example, comprise a plastic resin substrate 48 that is clad with a metallic thermally conductive surface 46, such as copper, nickel, stainless steel, etc. The substrate 48 of the mounting structure could be of the same material used for a printed circuit board with a copper cladding adhering over the surface. In the preferred embodiment, the mounting structure has the configuration of an X-shape with supporting arms extending diametrically across the cross-section air flow to thereby provide an average air flow temperature at the position of the supporting arms. As can be appreciated, the turbulence generated within the flexible hose and the possibility of laminar air flow can be neutralized by the X-shaped configuration so that the temperature measured will represent the mean average air temperature delivered to the thermal blanket 4.

The first sensor unit 36 and the sensor unit 38 may be any electrical or electronic device for temperature sensing, such as a thermal couple, thermistor, resistive temperature device (RTD), semiconductor dio-junction, or integrated circuit temperature sensor with and without integrated controller or signal conditioner. In the preferred embodiment shown herein, the first and second sensors are thermistors mounted at the junction or central point of the arms of the mounted structure 44.

Figure 6:
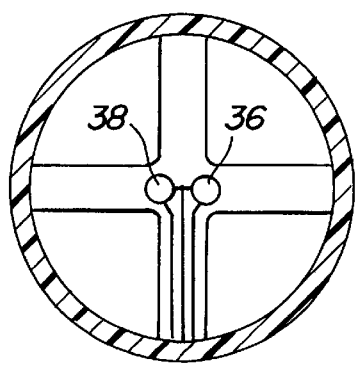
FIG. 6 is an elevated view of an alternative embodiment of the heat conductive support member for the temperature sensors.
Figure 7:
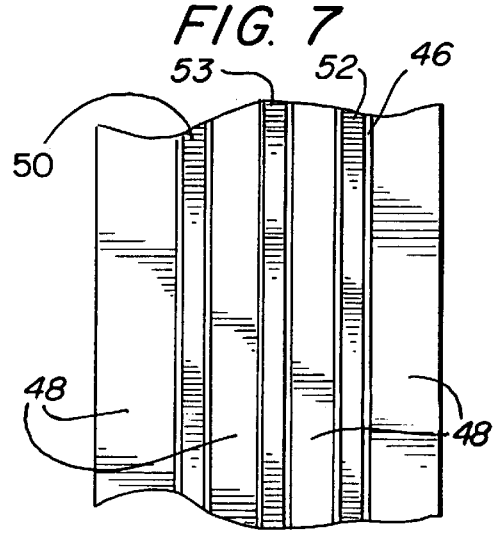
FIG. 7 is an expanded view of a portion of FIG. 6.

As can be appreciated, one of the arms of the mounting structure can actually be patterned with electrical connector line traces to electrically connect the thermal sensors to leads of a three-conductor cable. That is, three separate line traces could be used for providing connections for each of the respective first sensor 36 and second sensor 38. By use of a printed circuit substrate, an economical means of providing a rugged sensing structure, while also providing means for making an electrical connection to the sensors by cladding a heat transmitting metallic material, can be accomplished. FIGS. 6 and 7 show an arrangement of providing electrical connector lines 50, 52, and 53 for respective sensor units on the mounting structure 44. The three connectors provide power on line 53 and receive output signals on, respectively, lines 50 and 52.

Figure 9:
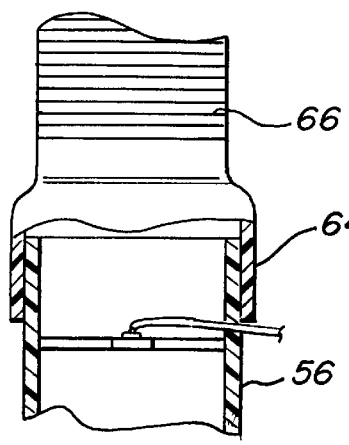
FIG. 9 is a cross-sectional view of the coupler port of the embodiment of FIG. 8.
Figure 8:
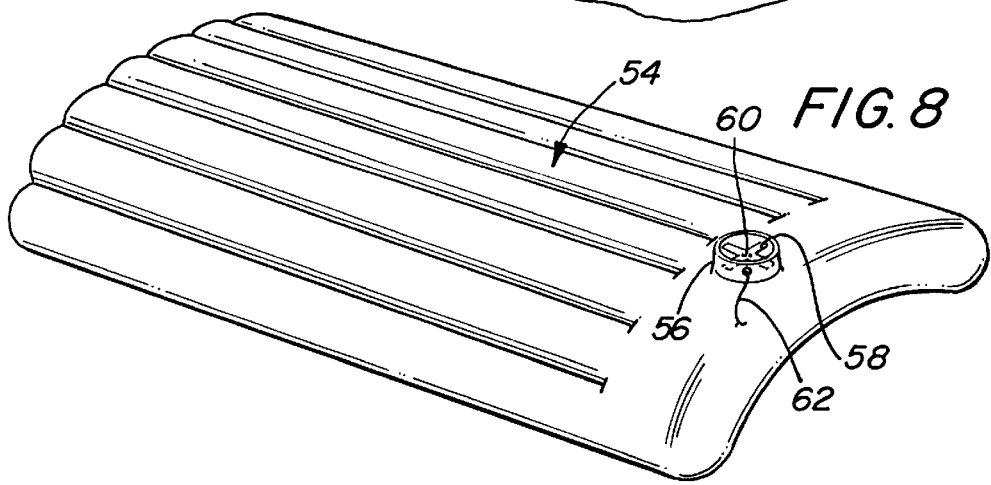
FIG. 8 is a perspective view of an alternative embodiment of the present invention disclosing the temperature sensor units mounted on a thermal blanket.

Another embodiment of the present invention is disclosed in FIG. 8 in the form of a thermal blanket 54 having a coupling port 56 of a cylindrical plastic configuration. Mounted within the coupling port 56 is a temperature sensor mounting structure 58 of a configuration, such as shown in FIGS. 6 and 7 or FIG. 4. A sensor unit, such as a thermistor 60, can be mounted at the junction of the mounting arms. Finally, electrical connector wires 62 can be interconnected with the console 18, such as shown in the embodiment of FIG. 2, or can be simply threaded through the length of the conduit line for connection with an internal receptacle adjacent the coupling port 32 and the console 18. FIG. 9 discloses a partial cross-sectional configuration of a coupling port 56 of the thermal blanket 54 with a coupler 64 on a flexible conduit 66.

Figure 10:
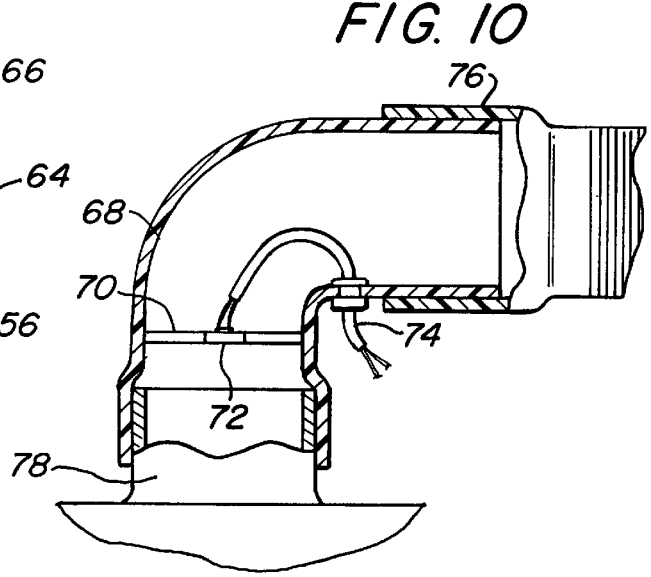
FIG. 10 is a side view of another embodiment of the temperature sensor unit mounted in a removable coupler unit.

Finally, referring to another alternative embodiment disclosed in FIG. 10, a coupler unit 68 can mount a mounting structure 70 supporting a sensor unit 72 with electrical line 74. Thus, the module coupler unit 68 can be removably connected to both a coupler 76 on a flexible hose and a coupling port 78 on a thermal blanket.

In each of the embodiments of the present invention, a temperature of the heated air can be measured as it is delivered to a thermal blanket, and the individual sensor or pair of sensors on a mounting structure can reside either directly attached to the thermal blanket, integrated with the flexible hose, or be in a separate modular coupler.

Figure 5:
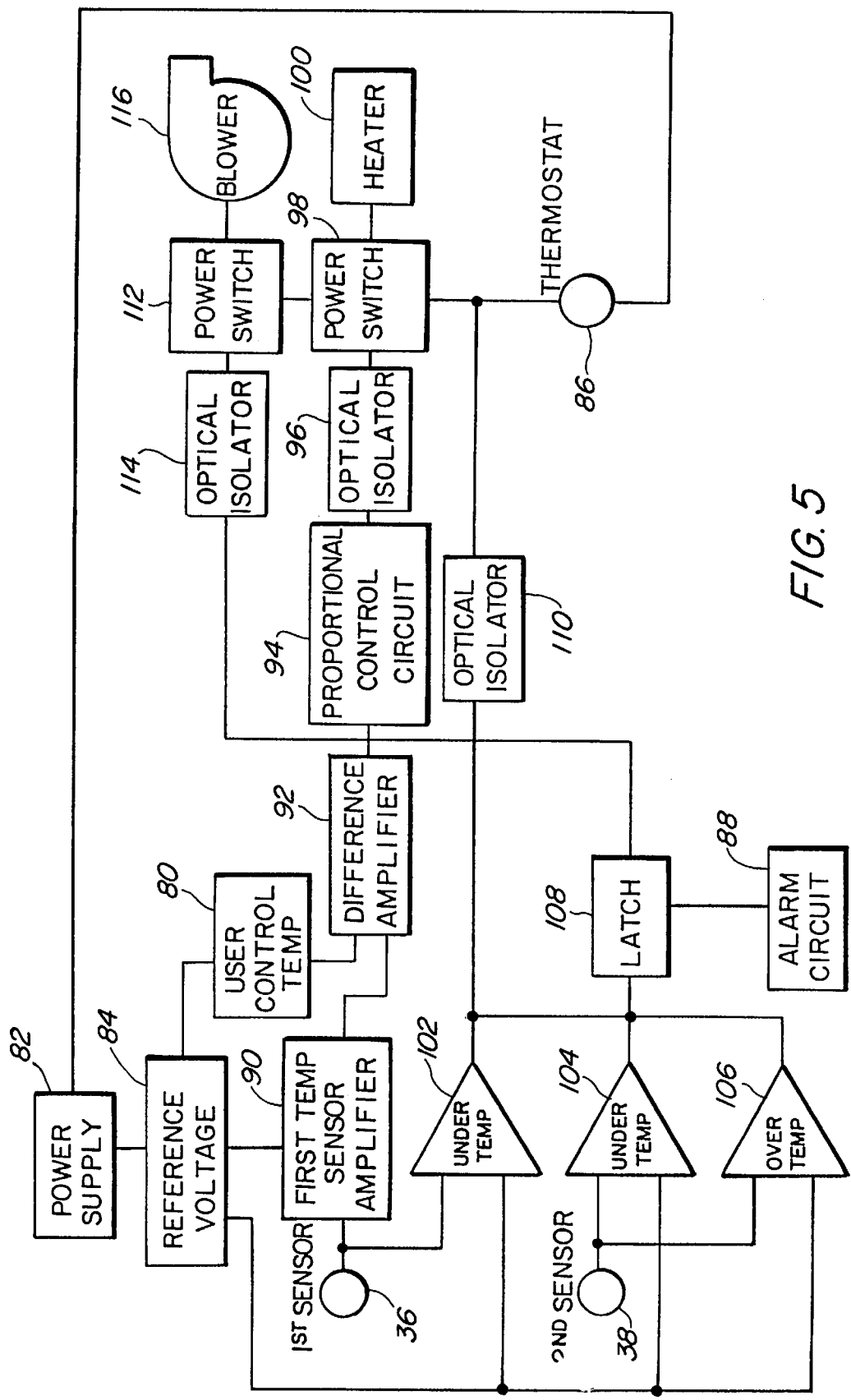
FIG. 5 is a schematic diagram of a control circuit.

Referring to FIG. 5, one possible schematic form of a control circuit is disclosed. Other forms of temperature control circuits can be used, as can be appreciated by a person of skill in this field. The specific control circuit 34 incorporates a proportional controller that includes an alarm system to permit a servo-controlling of the warmed air to a preset temperature level that will be set by the operator or user controls 20 on the housing of the console 18. In this schematic, the user control temperature setting 80 is connected to a power supply 82 through a reference voltage circuit 84 which also provides excitation current for the first and second sensor units 36 and 38. The reference voltage circuit 84 can divide and buffer the power source 82 on the control circuit. By providing two separate sensors 36 and 38, there is a redundancy in the system, and the control circuit 34 can thereby also sense the air temperature through the second thermistor or sensor unit 38, located in proximity to the first sensor unit 36 or thermistor to thereby provide a backup for any over temperature condition. As a safety feature of this control circuit, any over temperature sensed by the second sensor 38 or under temperature sensed by either the second sensor 38 or the first sensor 36 or the opening of an over temperature thermostat 86, which can be located in the heater housing or console 18, can turn off the blanket warming system. Thus, any of these conditions of an over temperature or an under temperature will indicate a problem and can be utilized to automatically shut off the power to the heater unit 28 and the blower 26 and to also further activate audible and visual alarms in the alarm circuit 88.

The first temperature sensor 36 amplifies the sensed voltage that is proportional to the air temperature adjacent a thermal blanket that is receiving the delivered heated air. This temperature signal is amplified in a first temperature sensor amplifier 90. The amplified temperature signal is subtracted from a set point temperature from the user control temperature 80 by a differential amplifier or a difference amplifier circuit 92. The resulting output difference signal is provided to a proportional control circuit 94, and this different signal is compared to a triangular wave that is generated to provide a pulse width modulated (PWM) signal whose duty cycle is proportional to the difference in the output temperature and the set point temperature provided by the user control temperature 80. This WPM signal is then applied to a solid state power switch circuit 98 through an optical isolator 96. The power switch circuit 98 delivers appropriate pulses to the heater unit 100.

An alarm detection circuit includes under temperature comparator 102, under temperature comparator 104, and over temperature comparator 106. The output of these comparators 102, 104, and 106 are output together and inverted to be coupled to a reset input of a latch circuit 108. Additionally, the voltage across the thermostat 86 is also applied to the latch reset through an optical isolator 110. If either the first sensor thermistor 36 or the second sensor thermistor 38 senses a very low temperature, which may occur in the case of an open sensor or the second sensor 38 senses an over temperature, or if the thermostat 86 itself mechanically breaks or opens, the latch circuit 108 is reset and opens a second solid state power switch circuit 112 that is also optically isolated by an optical isolator 114. The power switch circuit 112 is in series with the heat control power switch circuit 98, and the power switch 112 controls power to the blower unit 116, as well as the heater 100, and has the capacity of shutting down the entire warming system until this alarm condition is corrected, and the warming system is reset by turning off the power and turing the power back on. The thermostat 86 is in series with both of these solid state power switches 112 and 98 and can positively interrupt power to both the heater unit 100 and the blower unit 116. The output of the latch circuit 108 can also turn on a transistor to activate both audible and visual alarms in an alarm circuit 88.

While applicants have chosen a preferred control circuit, the embodiments of the present invention can also be operated with alternative control circuits.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A fluid blanket warming system for a patient comprising:
    a blanket unit having an approximately hollow core for receiving a gas and a coupling port to enable the admission of gas;
    a heater unit for heating the gas;
    a blower unit for forcing gas to the heater unit;
    a control circuit for controlling the temperature of the heater;
    a flexible conduit for delivery of the heated gas to the blanket unit;
    a temperature sensor unit mounted adjacent the blanket unit and in contact with the gas exiting the flexible conduit from the heater unit to provide a temperature signal, representative of the heated gas delivered to the blanket unit, to the control circuit whereby the heater unit can be controlled to a predetermined temperature for a patient; and
    a coupler for connecting the conduit with the blanket unit, the temperature sensor unit is mounted on the coupler.

2. A blanket warming system as in claim 1 wherein the coupler has a housing for connection with the coupling port and a heat conductive member extending across a flow path of the heated gas.

3. A blanket warming system as in claim 2 wherein the heat conductive member mounts the temperature sensor.

4. A blanket warming system as in claim 3 wherein the heat conductive member has a plurality of arm members with the temperature sensor mounted at an interconnection of the arm members.

5. A blanket warming system as in claim 2 wherein the heat conductive member has a plastic resin substrate and is clad with a heat conductive metal.

6. A blanket warming system as in claim 5 wherein the temperature sensor unit is electrically connected to a portion of the heat conductive metal.

7. A blanket warming system as in claim 1 further including a second temperature sensor unit mounted adjacent the blanket unit and connected to the control circuit.

8. A fluid blanket warming system as in claim 1, wherein the temperature sensor unit includes a connector extending along an interior of the conduit for connection to the control circuit.

9. An improved air warming system for providing a controlled temperature of air to an air blanket comprising:
    a housing with an inlet for ambient air;
    a heater unit for heating air in the housing;
    a blower unit for forcing air to the heater unit;
    a control circuit for controlling the temperature of the heater;
    a remote temperature sensor unit for mounting adjacent the air blanket to provide a temperature signal representative of the average temperature of the heated air delivered to the air blanket to the control circuit whereby the heater unit can be controlled to a predetermined temperature for a patient; and
    a coupler for connecting with the air blanket the remote temperature sensor is mounted on the coupler.

10. An improved air warming system as in claim 9 wherein the coupler has a housing for connection with the coupling port and a heat conductive member extending across a flow path of the heated air.

11. An improved air warming system as in claim 10 wherein the heat conductive member mounts the temperature sensor.

12. An improved air warming system as in claim 10 wherein the heat conductive member has a plurality of arm members with the temperature sensor mounted at an interconnection of the arm members.

13. An improved air warming system as in claim 10 wherein the heat conductive member has a plastic resin substrate and is clad with a heat conductive metal.

14. An improved air warming system as in claim 13 wherein the temperature sensor unit is electrically connected to a portion of the heat conductive metal.

15. An air blanket warming system as in claim 14 further including a second temperature sensor unit mounted adjacent the air blanket unit and connected to the control circuit.

16. An improved air warming system as in claim 9, wherein the temperature sensor unit includes a connector extending along an interior of the conduit for connection to the control circuit.

17. An improved air warming system as in claim 9, wherein the temperature sensor mounting structure enables the temperature sensor to measure a average temperature across a flow path of heated air.

18. An improved air warming system as in claim 17, wherein the temperature sensor mounting structure includes a heat conductive metal that extends across the flow path of heated air from approximately an interior surface of the conduit to a center of the conduit.

19. A remote temperature sensor unit for providing a measurement of warm air to be delivered to a patient by an air blanket connected to a heater unit, comprising:

a temperature sensor for proving a temperature signal; and a support member configured for direct connection to the air blanket and supporting the temperature sensor to measure the average temperature of the warm air as it is delivered to the air blanket, including a heat conductive member operatively connected to the temperature sensor and extending across a flow area of the warm air.

20. A conduit unit for fluidly interconnecting an air blanket with a housing with a heater unit having a control circuit for controlling the temperature of the heater unit, comprising:

an elongated flexible conduit having a first coupler at one end of the conduit configured for removable connection to the housing and a second coupler at the other end of the conduit configured for removable connection to the air blanket;

a temperature sensor mounted to sense the temperature of the air heated by the heater unit as it exits the second coupler; and an electric connector extending from the temperature sensor through an interior of the elongated flexible conduit to the second coupler and having an end portion adapted to be electrically connected to transmit a temperature signal from the temperature sensor to the control circuit whereby the heater unit can be controlled to a predetermined temperature for a patient.

21. A conduit unit as in claim 20, wherein the temperature sensor measures a mean average temperature across a flow path of the heated air.

22. A conduit unit as in claim 21, further including a heat conductive mounting structure for supporting the temperature sensor, the mounting structure extends across the flow path to provide an average of a temperature profile of the heated air.

23. A fluid blanket warming system for a patient comprising:

a blanket unit having an approximately hollow core for receiving a gas and a coupling port to enable the admission of gas;

a heater unit for heating the gas;

a blower unit for forcing gas to the heater unit;

a control circuit for controlling the temperature of the heater unit;

a conduit for delivery of the heated gas to the blanket unit;

a coupler for connecting the conduit with the coupling port of the blanket unit;

a heat conductive member is mounted on the coupler to extend across a flow path of the heated gas; and a temperature sensor unit is mounted on the coupler in thermal contact with the heat conductive member to provide a temperature signal, representative of the heated gas delivered to the blanket unit, to the control circuit whereby the heater unit can be controlled to a predetermined temperature for a patient.

24. A fluid blanket warming system as in claim 23 wherein the heat conductive member mounts the temperature sensor.

25. A fluid blanket warming system as in claim 23 wherein the heat conductive member has a plurality of arm members with the temperature sensor mounted at an interconnection of the arm members.

26. A fluid blanket warming system as in claim 23 wherein the heat conductive member has a plastic resin substrate and is clad with a heat conductive metal.

27. A fluid blanket warming system as in claim 26 wherein the temperature sensor unit is electrically connected to a portion of the heat conductive metal.

28. A fluid blanket warming system as in claim 23 further including a second temperature sensor unit mounted adjacent the blanket unit and connected to the control circuit.

29. A conduit unit for fluidly interconnecting an air blanket with a housing with a heater unit having a control circuit for controlling the temperature of the heater unit to deliver heated air to the air blanket, comprising:

an elongated flexible conduit having a first coupler at one end of the conduit configured for removable connection to the housing and a second coupler at the other end of the conduit configured for removable connection to the air blanket;

a mounting structure positioned on the second coupler for extending across a flow path of the heated air to provide a temperature of a mean air temperature;

a temperature sensor mounted on the mounting structure to sense the mean air temperature and output a representative signal; and means for connecting the output of the temperature sensor to the control circuit.

30. A conduit unit as in claim 29, wherein the means for connecting includes an electrical connector extending in the elongated flexible conduit between the first coupler and the second coupler.

31. A conduit unit as in claim 29, wherein the mounting structure also provides an electrical connection to the temperature sensor.

32. A conduit unit as in claim 31, wherein the mounting structure includes a heat conducting metal coating.

* * * * *

(12) EX PARTE REEXAMINATION CERTIFICATE (4993rd)
United States Patent
Shigezawa et al.

(10) Number: US 6,143,020 C1
(45) Certificate Issued: Sep. 28, 2004

(54) AIR WARMING SYSTEM FOR PROVIDING A CONTROLLED TEMPERATURE OF AIR TO AN AIR BLANKET

(75) Inventors: Gordon Shigezawa, Irvine, CA (US); Anthony V. Beran, Santa Ana, CA (US)

(73) Assignee: Respiratory Support Products, Inc., Irvine, CA (US)

Reexamination Request:
No. 90/006,444, Nov. 6, 2002

Reexamination Certificate for:
Patent No.: 6,143,020
Issued: Nov. 7, 2000
Appl. No.: 09/113,630
Filed: Jul. 10, 1998

(51) Int. Cl.[7] ............................. A61F 7/00; A61F 7/12
(52) U.S. Cl. ..................... 607/96; 607/104; 607/107
(58) Field of Search ........................ 607/96, 104, 107, 607/108, 112; 165/46; 126/204; 5/423

(56) References Cited

U.S. PATENT DOCUMENTS 4,398,535 A * 8/1983 Guibert ..................... 607/107
6,143,020 A * 11/2000 Shigezawa et al. .......... 607/96

OTHER PUBLICATIONS

Bair Hugger® Patient Warming System, Model 200 Operation Manual, 1988.*
Bair Hugger® Patient Warming System, Service Manual, 1988.*
Nightingale, et al, "A New Method for Maintaining Body Temperature in Children", Anesthesiology, 65:447, 448, 1986.*

* cited by examiner

Primary Examiner—Michael Peffley

(57) ABSTRACT

A fluid blanket warming system for a patient includes a thermal blanket unit for receiving heated gas through a coupling port. A portable heat source includes a heater unit and a blower unit that are controlled by a control circuit for providing a desired output to temperature to a patient. A flexible conduit delivers the heated gas from the heat source to the thermal blanket. A temperature sensor unit can be mounted adjacent the thermal blanket unit and in contact with the gas received from the heater unit to provide a temperature signal representative of the heated gas. The temperature sensor unit can be mounted directly on the thermal blanket, on the coupler of the flexible conduit, or on a modular coupler to provide a temperature signal to the control circuit.

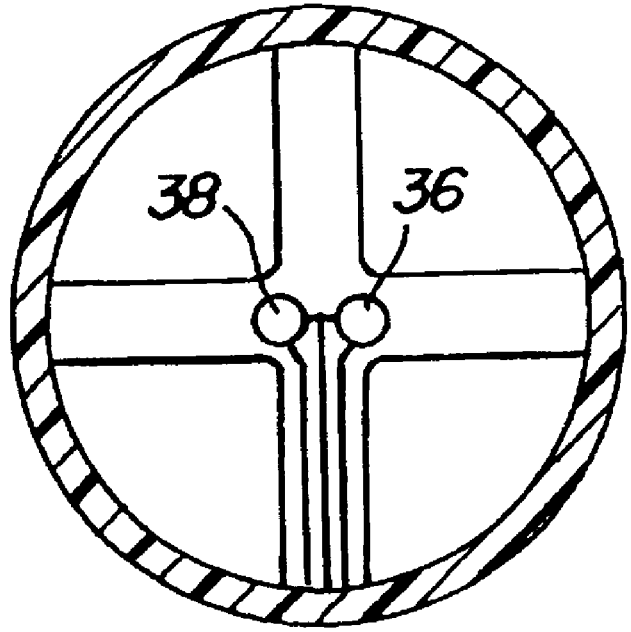

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 21 and 22 are cancelled.

Claims 1, 2, 9, 19, 20, 23 and 29 are determined to be patentable as amended.

Claims 3–8, 10–18, 24–28 and 30–32, dependent on an amended claim, are determined to be patentable.

1. A fluid blanket warming system for a patient comprising:
    a blanket unit having an approximately hollow core for receiving a gas and a coupling port to enable the admission of gas;
    a heater unit for heating the gas;
    a blower unit for forcing gas to the heater unit;
    a control circuit for controlling the temperature of the heater;
    a flexible conduit for delivery of the heated gas to the blanket unit;
    a temperature sensor unit mounted adjacent the blanket unit *with a heat conductor member operatively connected to the temperature sensor unit and extending sufficiently across a cross-section of a flow path* and in contact with the gas exiting the flexible conduit from the heater unit to provide a *mean* average air temperature signal *from the temperature sensor unit*, representative of the heated gas delivered to the blanket unit, to the control circuit whereby the heater unit can be controlled to a predetermined temperature for a patient; and
    a coupler for connecting the conduit with the blanket unit, the temperature sensor unit is mounted on the coupler.

2. A blanket warming system as in claim 1 wherein the coupler has a housing for connection with the coupling port [and a heat conductive member extending across a flow path of the heated gas].

9. An improved air warming system for providing a controlled temperature of air to an air blanket comprising:
    a housing with an inlet for ambient air;
    a heater unit for heating air in the housing;
    a blower unit for forcing air to the heater unit;
    a control circuit for controlling the temperature of the heater;
    a remote temperature sensor unit for mounting adjacent the air blanket to provide a temperature signal representative of the *mean* average temperature of the heated air *of the entire cross-section of air flow* delivered to the air blanket to the control circuit whereby the heater unit can be controlled to a predetermined temperature for a patient; and
    a coupler for connecting with the air blanket the remote temperature sensor is mounted on the coupler.

19. A remote temperature sensor unit for providing a measurement of warm air to be delivered to a patient by an air blanket connected to a heater unit, comprising:
    a temperature sensor for [proving] *providing* a temperature signal; and
    a support member configured for direct connection to the air blanket and supporting the temperature sensor to measure [the] *a mean* average temperature of the warm air as it is delivered to the air blanket, including a heat conductive member operatively connected to the temperature sensor and extending across a *cross-section of* flow area of the warm air *to enable the temperature sensor to monitor the mean average air temperature of the cross-section of air flow delivered to the air blanket*.

20. A conduit unit for fluidly interconnecting an air blanket with a housing with a heater unit having a control circuit for controlling the temperature of the heater unit, comprising:
    an elongated flexible conduit having a first coupler at one end of the conduit configured for removable connection to the housing and a second coupler at the other end of the conduit configured for removable connection to the air blanket;
    a temperature sensor mounted to sense the temperature of the air heated by the heater unit as it exits the second coupler; [and]
    an electric connector extending from the temperature sensor through an interior of the elongated flexible conduit to the second coupler and having an end portion adapted to be electrically connected to transmit a temperature signal from the temperature sensor to the control circuit whereby the heater unit can be controlled to a predetermined temperature for a patient; *and*
    *a heat conductive mounting structure for supporting the temperature sensor, the mounting structure extends across the cross-section of the flow path to provide a mean average of a temperature profile of a cross-section of the heated air flow delivered to the patient.*

23. A fluid blanket warming system for a patient comprising:
    a blanket unit having an approximately hollow core for receiving a gas and a coupling port to enable the admission of gas;
    a heater unit for heating the gas;
    a blower unit for forcing gas to the heater unit;
    a control circuit for controlling the temperature of the heater unit;
    a conduit for delivery of the heated gas to the blanket unit;
    a coupler for connecting the conduit with the coupling port of the blanket unit;
    a heat conductive member is mounted on the coupler to extend across *a cross-section of* a flow path of the heated gas; and
    a temperature sensor unit is mounted on the coupler in thermal contact with the heat conductive member to provide a *mean* average temperature signal, representative of the *cross-section of the* heated gas delivered to the blanket unit, to the control circuit whereby the heater unit can be controlled to a predetermined temperature for a patient.

29. A conduit unit for fluidly interconnecting an air blanket with a housing with a heater unit having a control circuit for controlling the temperature of the heater unit to deliver heated air to the air blanket, comprising:

an elongated flexible conduit having a first coupler at one end of the conduit configured for removable connection to the housing and a second coupler at the other end of the conduit configured for removable connection to the air blanket;

a mounting structure positioned on the second coupler for extending across a *cross-section of a* flow path of the heated air to provide [a temperature] *an indication* of a mean air temperature *of delivered heated air*;

a temperature sensor mounted on the mounting structure to sense the mean air temperature *from the mounting structure* and output a representative signal; and means for connecting the output of the temperature sensor to the control circuit.

\* \* \* \* \*